(12) United States Patent
Sudo et al.

(10) Patent No.: US 7,766,882 B2
(45) Date of Patent: Aug. 3, 2010

(54) SYRINGE PISTON

(75) Inventors: Morihiro Sudo, Sumida-ku (JP); Tsuyoshi Koshidaka, Sumida-ku (JP)

(73) Assignee: Daikyo Seiko, Ltd., Tokyo (JP)

( * ) Notice: Subject to any disclaimer, the term of this patent is extended or adjusted under 35 U.S.C. 154(b) by 56 days.

(21) Appl. No.: 11/292,343

(22) Filed: Dec. 2, 2005

(65) Prior Publication Data
US 2006/0178643 A1    Aug. 10, 2006

(30) Foreign Application Priority Data
Dec. 27, 2004    (JP) ............... 2004-376478

(51) Int. Cl.
*A61M 5/315* (2006.01)
(52) U.S. Cl. .................. 604/218; 604/230
(58) Field of Classification Search ......... 604/218–222, 604/230
See application file for complete search history.

(56) References Cited

U.S. PATENT DOCUMENTS

| 6,213,985 B1 | 4/2001 | Niedospial, Jr. |
| 6,511,459 B1 | 1/2003 | Fago |
| 2001/0056264 A1 | 12/2001 | Sayama et al. |
| 2005/0137533 A1* | 6/2005 | Sudo et al. .......... 604/218 |

FOREIGN PATENT DOCUMENTS

| EP | 0 841 374 A2 | 5/1998 |
| EP | 0879611 | 5/1998 |
| EP | 1 547 633 A1 | 6/2005 |
| JP | 57-22766 | 2/1982 |
| JP | 7-124257 | 5/1995 |
| JP | 7-213611 | 8/1995 |
| JP | 2003-190285 | 7/2003 |
| JP | 2003190285 A * | 7/2003 |
| WO | WO 2004/075958 A2 | 9/2004 |

OTHER PUBLICATIONS

Office Action from European Patent App. No. 05026270.8 (Jul. 26, 2007).

* cited by examiner

*Primary Examiner*—Nicholas D Lucchesi
*Assistant Examiner*—Theodore J Stigell
(74) *Attorney, Agent, or Firm*—Kenealy Vaidya LLP

(57) ABSTRACT

A rubber-made syringe piston with a film laminated on it includes a plurality of annular ridges of different outer diameters formed continuously and integrally on a sliding surface of a liquid-contacting, leading end portion of the piston. The annular ridges may preferably be different by from 0.01 to 0.2 mm from one to another in outer diameter.

8 Claims, 4 Drawing Sheets

SYRINGE PISTON

FIELD OF THE INVENTION

This invention relates to a piston useful in a syringe for a medicine or medical care, and more specifically to a syringe piston having high sealing property even when a liquid medicine of high penetrating property is filled in a syringe.

DESCRIPTION OF THE BACKGROUND

A piston for a medicine syringe or medical syringe is required to have no interaction with a liquid medicine to be filled in a syringe barrel and further, to be equipped with the mutually contradictory properties (performances) of sealing property and sliding property within the syringe barrel. For pistons to be used in pre-filled syringes (in other words, container syringes) which contain liquid medicines filled beforehand therein and are finding increasing utility in recent years, these properties are required at still higher levels than those required for conventional syringe pistons. Pistons for such pre-filled syringes are, therefore, required to keep quality unchanged, to permit safe use over long term, to assure sealing property (safety) even for liquid medicines of high penetrating property, and moreover, to possess a similar level of sliding property as in conventional syringes.

With a view to meeting such requirements, some approaches have been proposed to date, including: externally fitting one or more ring members such as O-rings on a main body of a plastic-made piston to form a corresponding number of sliding surfaces (at which the piston is to be brought in contact with the inner wall of a syringe barrel) (JP-A-07-213611); providing plural annular seal portions in the form of ribs on a sliding surface to form annular grooves between the adjacent annular seal portions (JP-A-07-124257); and limiting an area of contact of a piston with a syringe barrel and the compression factor of the piston to specific ranges, respectively (JP-A-57-022766). These proposed approaches are, however, all insufficient to satisfy both sealing property and sliding property for liquid medicines of high penetrating property.

In the meantime, the present inventors disclosed, as a piston capable of achieving both high sealing property and sliding property for liquid medicines of such high penetrating property, a syringe piston that features at least one annular microgroove formed on a sliding surface of a liquid-contacting, leading end portion of the piston (JP-A-2003-190285). With this piston, however, lamination of a film on the surface of the piston results in the formation of wrinkles in the film on the surface of the piston due to a difference in shrinkage factor between a rubber material as a material of the piston main body and the material of the film laminated on the surface of the piston when the piston shrinks beyond a certain level. In some instances, the liquid medicine may therefore leak out through crevasses formed by and along the wrinkles. There is, accordingly, an outstanding desire for further improvements.

SUMMARY OF THE INVENTION

With the foregoing circumstances in view, the present invention has been completed. An object of the present invention is, therefore, to provide a syringe piston having high sealing property and sliding property even when used as a piston for a pre-filled syringe with a liquid medicine of high penetrating property filled therein.

The above-described object can be achieved by the present invention, the constitution of which is described as follows:

1) A rubber-made syringe piston with a film laminated thereon, comprising a plurality of annular ridges of different outer diameters formed continuously and integrally on a sliding surface of a liquid-contacting, leading end portion of the piston.

2) A rubber-made syringe piston as described above in 1), wherein the annular ridges are different by from 0.01 to 0.2 mm from one to another in outer diameter.

3) A rubber-made syringe piston as described above in 1), wherein the film is made of a fluorinated resin.

According to the present invention, the syringe piston has high sealing property and reduced sliding resistance even when used as a piston for a pre-filled syringe with a liquid medicine of high penetrating property filled therein. Owing particularly to the plural annular ridges of different outer diameters formed continuously on the leading end portion of the piston, one of the annular ridges, said one ridge having an optimal diameter, can still retain sealing property even when there is an unavoidable dimensional manufacturing error in the inner diameter of a syringe barrel and/or the outer diameter of the piston. Despite such dimensional manufacturing error or errors in the above-described members, the syringe piston according to the present invention can retain high sealing property.

DETAILED DESCRIPTION OF THE INVENTION AND PREFERRED EMBODIMENTS

Based on certain preferred embodiments, the present invention will hereinafter be described in further detail.

For the manufacture of the syringe piston according to the present invention for a medicine or medical care, which may herein after be simply called "piston" for the sake of brevity, any one of rubber materials which have been employed for the manufacture of pistons can be used, and no particular limitation is imposed in this respect.

Examples of usable rubber materials include butyl rubbers such as butyl rubber, chlorinated butyl rubber, brominated butyl rubber, and divinylbenzene-copolymerized butyl rubber; conjugated diene rubbers such as polyisoprene rubber (high to low cis-1,4 bond), polybutadiene rubber (high to low cis-1,4 bond), and styrene-butadiene copolymer rubber; and ethylene-propylene-diene terpolymer rubber (EPDM).

Using a crosslinkable rubber composition (compound) obtained by kneading the above-described rubber material together with additives such as a crosslinking agent, a filler and/or reinforcement, a colorant and an age resister, the piston according to the present invention can be manufactured by a conventionally-known piston-forming process such as compression molding or injection molding. As additives to be used, those conventionally employed in the manufacture of rubber plugs or pistons for medicines or medical devices are all usable, and no particular limitation is imposed thereon.

The syringe piston according to the present invention may desirably be laminated at surfaces thereof, where the syringe piston is brought into contact with a liquid medicine and is brought into sliding contact with the inner wall of an associated syringe barrel, with a plastic film of a fluorinated resin, ultra-high-molecular-weight polyethylene, polyethylene, polypropylene, a polyester or nylon (namely, a plastic-laminated piston). From the standpoint of providing the liquid-contacting portion of the piston with stability, water repellency and the like, it is particularly desired to cover at least the liquid-contacting portion of the piston with a fluorinated resin film. It is to be noted that as the "fluorinated resin" in the present invention, PTFE (polytetrafluoroethylene), ETFE (ethylene-tetrafluoroethylene copolymer), PFA (perfluoroalkoxyalkane), FEP (perfluoroethylene/propylene copolymer), PVDF (polyfluorinated vinylidene), and their polymer alloys with other polymers can be selectively used as desired.

The syringe piston according to the present invention is exactly the same as the conventional pistons insofar as its raw material, that is, its rubber material and its manufacturing process are concerned. It is, however, characterized in that the plural annular ridges of different outer diameters are formed continuously and integrally on the sliding surface of the liquid-contacting, leading end portion of the piston.

Figure 1A:
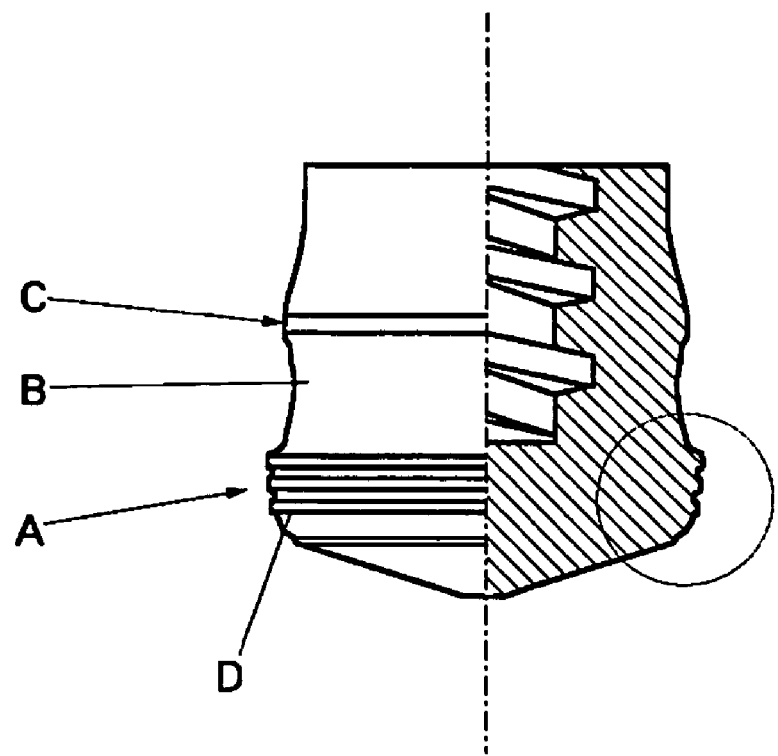
FIG. 1A is a cross-sectional/side view of a syringe piston according to one embodiment of the present invention.
Figure 1B:
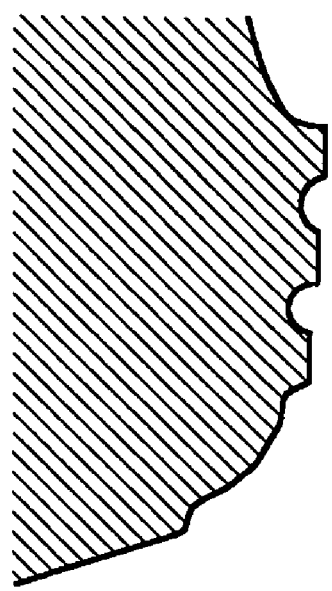
FIG. 1B is an enlarged cross-sectional view of a section encircled by an alternate long and short dash line in FIG. 1A.

One embodiment will now be described with reference to some of the accompanying drawings. The piston shown in FIG. 1A is formed by way of example such that the piston has the maximum diameter at its liquid-medicine-contacting, leading end portion and a somewhat smaller diameter on a side, where it is connected threadedly or in another fashion with a plunger (piston rod), to present a tapered profile as a whole (it is however to be noted that its maximum diameter is greater than the inner diameter of the associated syringe barrel). The right-hand half of FIG. 1A is a cross-sectional view, while the left-hand half of the same drawing is a side view. Sliding surfaces A, C are formed flat and smooth to assure their contact with the inner wall of the syringe barrel, but a surface B is formed to define a circular arc recess and remains out of contact with the inner wall of the syringe barrel. FIG. 1B is an enlarged cross-sectional view of a section encircled by an alternate long and short dash line in FIG. 1A.

Annular ridges D, which constitute the characteristic feature of the present invention, are formed as many as three on the sliding surface A of the liquid-contacting, leading end portion of the piston in the illustrated embodiment, although the syringe piston according to the present invention can be provided with two or more of such annular ridges. No particular limitation is imposed on the cross-sectional shape of each annular ridge, and a semi-spherical, semi-elliptic, rounded rectangular or like cross-sectional shape can be mentioned as an example. However, a cross-sectional shape capable of creating a large area of contact with the syringe barrel is desired. Specifically, a rounded rectangular cross-sectional shape, a semi-elliptic cross-sectional shape and a semi-spherical cross-sectional shape becomes less preferred in this order. The dimensions of each annular ridge, specifically its width in the direction of the length of the piston and its height from the sliding surface of the leading end portion of the piston vary depending on the size of the piston (i.e., its diameter and the length of its sliding surface), and can be hardly specified in a wholesale manner. In general, however, the width may range approximately from 0.05 to 0.5 mm, while the height may range approximately from 0.02 to 0.3 mm. The intervals between the adjacent annular ridges can be set, as an indication, substantially equal to the width of each annular ridge. Concerning the width and height of each annular ridge and the intervals of the adjacent annular ridges, it is necessary to determine optimal values in accordance with the size of the piston and also by taking into consideration the manufacturing accuracy of a mold. The number of annular ridges also differs depending on the size of the piston and the length of the sliding surface, and therefore, can be hardly specified in a wholesale manner. It is, however, preferred to provide annular ridges as many as needed to account for 60% or less, preferably 40% or less of the entire length of the sliding surface. It is to be noted that the expression "the entire length of the sliding surface" as used herein does not mean the total length of only the sliding (i.e., contacting) parts of the piston, where the piston slides on (i.e., contacts to) the syringe barrel, but means the entire length of the side wall of the piston on its sliding side (in other words, the entire length of the piston). An excessively small number of annular ridges, in other words, the arrangement of only one annular ridge cannot bring about the advantageous effects of the present invention sufficiently, while an unduly large number of annular ridges leads to a reduction in sliding property.

Figure 2:
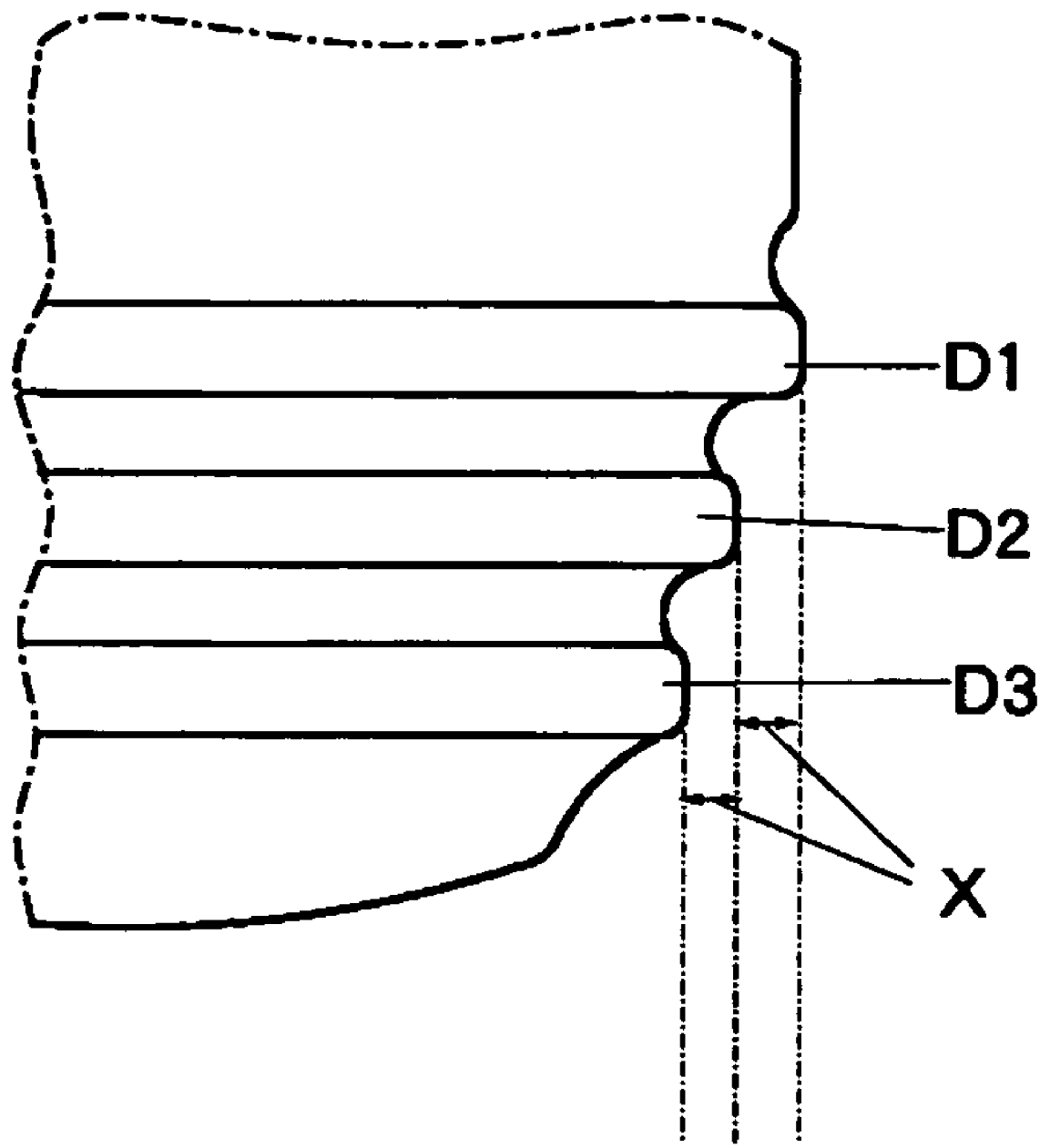
FIG. 2 is an enlarged fragmentary side view of the encircled section of FIG. 1A.
Figure 3A:
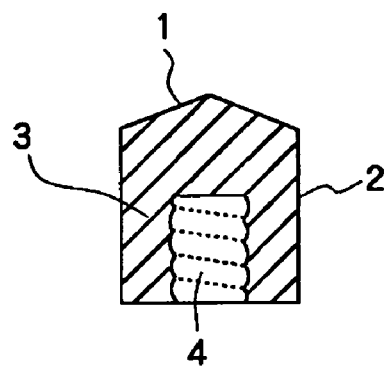
FIG. 3A is a schematic cross-sectional view showing the configurations of a piston (without annular ridges) according to a first modification of the embodiment of the present invention.
Figure 3B:
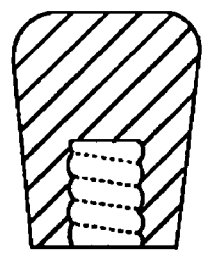
FIG. 3B is a schematic cross-sectional view showing the configurations of a piston (without annular ridges) according to a second modification of the embodiment of the present invention.
Figure 3C:
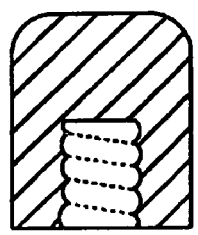
FIG. 3C is a schematic cross-sectional view showing the configurations of a piston (without annular ridges) according to a third modification of the embodiment of the present invention.
Figure 3D:
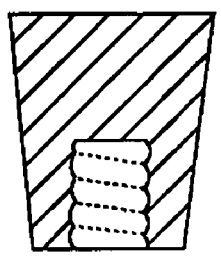
FIG. 3D is a schematic cross-sectional view showing the configurations of a piston (without annular ridges) according to a fourth modification of the embodiment of the present invention.
Figure 3E:
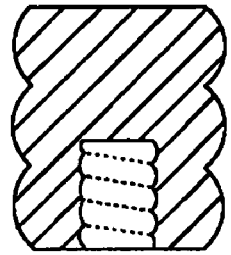
FIG. 3E is a schematic cross-sectional view showing the configurations of a piston (without annular ridges) according to a fifth modification of the embodiment of the present invention.
Figure 3F:
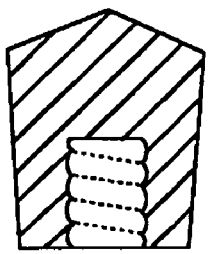
FIG. 3F is a schematic cross-sectional view showing the configurations of a piston (without annular ridges) according to a sixth modification of the embodiment of the present invention.
Figure 3G:
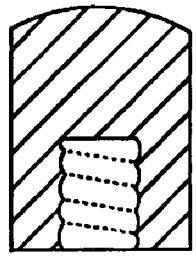
FIG. 3G is a schematic cross-sectional view showing the configurations of a piston (without annular ridges) according to a seventh modification of the embodiment of the present invention.
Figure 3H:
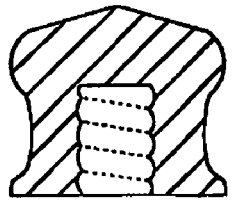
FIG. 3H is a schematic cross-sectional view showing the configurations of a piston (without annular ridges) according to an eighth modification of the embodiment of the present invention.
Figure 3I:
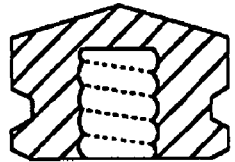
FIG. 3I is a schematic cross-sectional view showing the configurations of a piston (without annular ridges) according to a ninth modification of the embodiment of the present invention.

As illustrated especially in FIG. 2 which is an enlarged fragmentary side view of the encircled section of FIG. 1A, it is desired to provide the outer diameters of the mutually-adjacent annular ridges with differences (X). The provision of such differences allows one of the annular ridges to remain in contact with the inner wall of the syringe barrel to maintain sealing property even when there is an avoidable dimensional manufacturing error in the piston or a similar error in the inner diameter of the syringe barrel. It is, of course, necessary to make the height (diameter, D1) of the highest annular ridge (of the largest diameter) greater than the inner diameter of the syringe barrel. Owing to the elasticity of the rubber-made piston, no problem arises although the dimension of the annular ridge of the largest diameter is greater than the inner diameter of the syringe barrel.

Concerning the difference in diameter between a syringe barrel and its associated piston that can maintain optimal sealing property, a large tolerance is available when the piston is not a film-laminated piston. In the case of a film-laminated piston, however, this tolerance is limited to a very narrow range because the film is harder than rubber. Described specifically, when the diameter of the piston is excessively large compared with the inner diameter of the syringe barrel, wrinkles occur in the film on the surface of the piston, thereby impairing the sealing property. Owing to the arrangement of the plural annular ridges with differences in their heights, that is, outer diameters, one of the annular ridges can be brought into close contact with the inner wall of the syringe barrel so that the sealing property is not impaired.

The adaptability of the syringe piston according to the present invention to syringe barrels of varied inner diameters has been described in the above. Upon manufacturing a rubber-made piston, an avoidable error can obviously occur in the outer diameter of the piston because of the elastic nature of rubber. Even for such an error in the outer diameter of the piston, the sealing property is not impaired despite the error owing to the arrangement of the annular ridges. The differences (X) in height among the plural annular ridges cannot be specified in a wholesale manner, but differences of from about 0.01 to 0.2 mm or so are suited. Owing to the arrangement of two or more (preferably three or more) annular ridges, the problems of the unavoidable error upon manufacturing a piston and the problem based on a variation in the inner diameter of a syringe barrel can be resolved. It is desired to form the annular ridges such that, as illustrated in FIG. 2, they are continuously and integrally formed with diameters sequentially increasing in a direction from a leading end section of the piston toward its trailing end section.

The syringe piston according to the present invention can have various configurations as illustrated as modifications in FIG. 3A through FIG. 3I. These modifications include one having plural flat and smooth surface areas in the sliding surface thereof and those having one or more convex portions such as semi-circular portions in vertical cross-section. These flat and smooth surface areas or convex portions may each be provided with one or more annular ridges. Importantly, however, the sliding surface of at least the liquid-contacting, leading end portion must be provided with plural annular ridges. When the piston in a pre-filled syringe is an intermediate piston that divides the interior of the syringe barrel into plural compartments, it is necessary to provide the piston with annular ridges at both end portions thereof because the piston will be kept in contact at both end portions thereof with the corresponding liquid medicines.

In general, it is at the leading end portion (liquid-medicine-contacting side) of the piston, said portion having the largest diameter, that a stress concentrates upon sliding the piston. Owing to deformations of the annular ridges, however, this concentrated stress is distributed so that the sliding resistance is lowered.

Figure 4A:
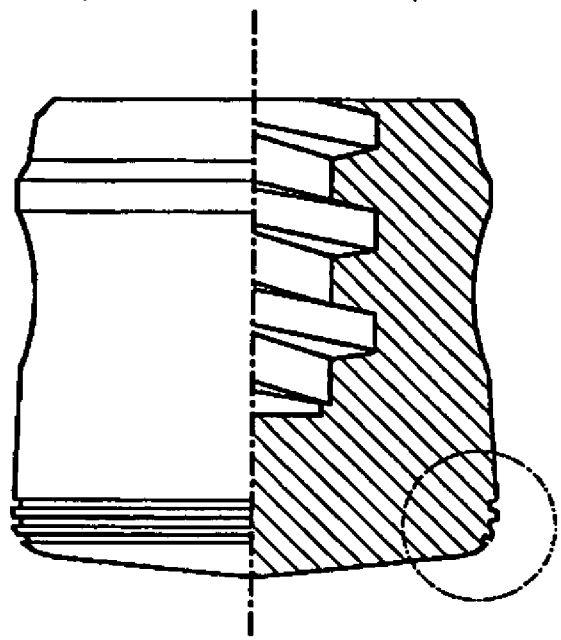
FIG. 4A is a cross-sectional/side view of a conventional syringe piston.
Figure 4B:
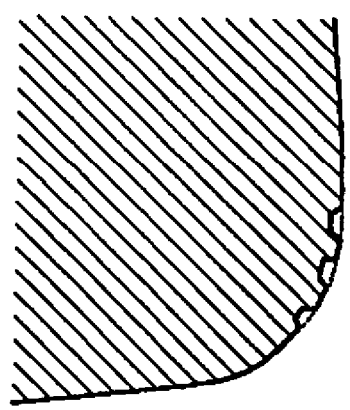
FIG. 4B is an enlarged cross-sectional view of a section encircled by an alternate long and short dash line in FIG. 4A.

The piston according to the present invention and the piston disclosed in JP-A-2003-190285 referred to in the above (see FIG. 4A and FIG. 4B) are similar to each other in external appearance. Described specifically, the piston disclosed in JP-A-2003-190285 is provided with one or more annular microgrooves on its liquid-contacting leading end portion. Where the piston is provided with plural annular microgrooves, one or more portions between the annular microgrooves have a structure similar to the annular ridges on the piston according to the present invention. However, the annular microgrooves are arranged on the surface of the piston disclosed in JP-A-2003-190285 so that the outer diameter or diameters of the portion or portions between the annular microgrooves is or are the same as the outer diameter of the ungrooved portion or portions of the piston. The piston disclosed in JP-A-2003-190285 is therefore provided with improved sealing property owing to the inclusion of the microgrooves as narrow slits in the sliding surface. At the sliding portion or portions, in other words, the portion or portions between the annular microgrooves, however, the piston disclosed in JP-A-2003-190285 only has the same sealing property as the outer diameter of the conventional piston.

The syringe piston according to the present invention, on the other hand, is provided at the sliding surfaces thereof with annular ridges. Portions between these ridges, therefore, exhibit similar effects as the piston disclosed in JP-A-2003-190285. Owing to the ridge portions greater in diameter than the conventional piston not provided with such annular ridges, the syringe piston according to the present invention can also exhibit still higher sealing property.

The syringe piston according to the present invention is useful in a conventional (disposable) syringe or pre-filled syringe the syringe barrel of which is formed of transparent, chemically-resistant and heat-resistant plastics (for example, polyethylene, polypropylene, cyclic polyolefin, polyester resin, polyamide resin, or the like). Pistons are classified into two types, one being pistons used in forms connected to plungers (i.e., piston rods), and the other being intermediate pistons for pre-filled syringes as described above. The present invention can be applied to both of these types. The configurations of the piston are diversified as described above, and no particular limitation is imposed thereon.

A lubricant can be applied to the sliding surface of the syringe piston according to the present invention as needed. In such a case, the lubricant may be applied over the entire sliding surface. It is, however, preferred to apply the lubricant specifically between the annular ridges, because the portions between the annular ridges function as reservoirs for the lubricant so that sufficient sliding property can be obtained with a coat amount smaller than a conventional coat amount. When the lubricant is employed, the penetration of liquid medicine onto the sliding surface of the piston is substantially blocked, and therefore, the sealing property is not affected despite the holding of the lubricant between the annular ridges.

As the lubricant, liquid fluoropolymers and the like can be used in addition to conventionally-used silicone oils. As the liquid fluoropolymers, any liquid fluoropolymers can be used irrespective of the molecular weights of their fluorine-containing monomers. Examples include low polymers of trifluoroethylene chloride, $(-CF_2CF(Cl)-)_n$; perfluoropolyether fluids $(CF_3(C_3F_6O)C_2F_5$, $CF_3-[(O-CF_2-CF_2)_p-OCF_2]_q-OCF_3$, etc.); and perfluoroalkylpolyethers $(F-[CF(CF_3)-CF_2O]-C_2F_5$, PFAE and PFPE).

From the market, they are available under the names of "DAIFLOIL™ #1" (product of Daikin Industries, Ltd., low polymers of trifluoroethylene chloride, $-(CF_2CF(Cl)-)_n$, average molecular weight: 500); "DEMNUM™ S—200" (product of Daikin Industries, Ltd., perfluoropolyether fluid $(-CF_2CF(Cl)-)_n$, average molecular weight: 8,400); "FOMBLIN™ Z" (product of Montefluos SpA, Italy, perfluoropolyether fluid $CF_3-[CF(CF_3)-CF_2O]_n-C_2F_5$, average molecular weight: 3,000); "FOMBLIN™ Y25" (product of Montefluos SpA, Italy, perfluoropolyether fluid $CF_3$—[(O—CF($CF_3$)—$CF_2$)$_n$—(O—$CF_2$)$_m$]—O—$CF_3$, average molecular weight: 3,000); "GALDEN™ D40" (product of Montefluos SpA, Italy, perfluoropolyether fluid $CF_3$—[(O—CF($CF_3$)—$CF_2$)—(O—$CF_2$)$_m$]—O—$CF_3$, average molecular weight: 1,550); "FLUORAD™ FC—732" (product of Sumitomo 3M Limited, hydrofluoroether); "KRYTOX™ AZ" (product of E.I. du Pont de Nemours and Company, U.S.A., perfluoroalkylpolyether F—[CF($CF_3$)—$CF_2OCF_2$]$_n$$CF_2CF_3$ (n=10 to 60), average molecular weight: 1,850).

EXAMPLES

The present invention will hereinafter be described more specifically based on Example and Comparative Example.

Example 1 & Comparative Example 1

Two types of syringe pistons were produced as many as twenty (20) per type with varied sizes. In each of the syringe pistons of one type (Example 1), a surface (sliding surface and liquid-medicine-contacting surface) made of chlorinated butyl rubber was laminated with a fluorinated resin film and had three annular ridges of the shape shown in FIGS. 1A, 1B and 2. In each of the syringe pistons of the other type (Comparative Example 1), on the other hand, a surface (sliding surface and liquid-medicine-contacting surface) made of chlorinated butyl rubber had three annular microgrooves shown in FIGS. 4A and 4B. The differences (X) in diameter between the adjacent annular ridges were set at 0.1 mm successively from the leading end portion of each piston.

A dummy solution was filled in pre-filled syringes made of a cyclic olefin polymer. Using the rubber-made pistons, they were tested for liquid sealing property and sliding property by the following methods.

(1) Liquid Sealing Property Test
A pressurization test partially following the "Standards for Medical Devices and Instruments—Standards for Sterilised Syringe Barrels", Notice No. P1079 issued Dec. 11, 1998 by the Director of Pharmaceutical and Food Safety Bureau, Ministry of Health, Labour and Welfare", Japan:

Clean plastic-made syringe barrels of various specified capacities were provided as many as twenty (20) for the syringes of each of Example 1 and Comparative Example 1. Rubber-made caps were applied to free ends (Luer portions) of the respective syringe barrels to seal them. A dummy solution, which had been prepared in accordance with the below-described formulation and had liquid nature of high penetrating property (colored with methylene blue), was poured as much as the specified capacities into the respective syringe barrels. Each of the syringe barrels had a resin film laminated extending from the side of its flange to its sliding surface and liquid-medicine-containing surface.

The rubber-made pistons as the invention products, each of which was equipped with the annular ridges formed thereon, and the rubber-made pistons as the comparative products, each of which was equipped with the annular microgrooves formed thereon, were gently pushed into the corresponding syringe barrels, and with the free ends of the syringe barrels directed upwards, the rubber caps were removed from the Luer portions. Into an internally-threaded portion on a side of an opening of each piston, a plastic-made plunger (piston rod) was threadedly inserted. The piston was gently pushed upwards to such a height that the liquid inside the syringe barrel still remained free from leakage, thereby pushing air out of the free end part of the syringe barrel. The rubber cap was put back to the Luer portion, and the syringe barrel was mounted on a measuring instrument for pressurization test. Pressurization conditions are shown in Table 1.

After a pressure specified for general medical applications was applied for 30 seconds, the syringe barrel was dismounted from the measuring instrument. An interfacial area between the piston and the syringe barrel was observed at ×10 magnification to determine whether or not any leakage of the aqueous solution of methylene blue had taken place to the sliding part. The results are shown in Table 2, in which the numbers of those developed liquid leakage among the corresponding 20 syringe barrels tested are shown.

[Preparation of Dummy Solution]
Anhydrous ethanol was added to a mixture of citric acid anhydride (2 g), "TWEEN™ 80" (polyoxyethylene diether, product of Imperial Chemical Industries PLC, U.K., 80 g) and "MACROGOL™ 400" (product of NOF Corporation, polyethylene glycol, molecular weight: 200 to 600, 650 g) to give a total volume of 1,000 mL. Further, methylene blue was added to prepare a methylene blue dummy solution of 0.1 wt./vol. % concentration.

TABLE 1

| Category | Capacity of syringe barrel (mL) | Pressure (kPa) |
|---|---|---|
| For general applications | Capacity < 3 | 392 |
| | 3 ≤ Capacity < 10 | 343 |
| | 10 ≤ Capacity < 20 | 294 |
| | 20 ≤ Capacity < 30 | 245 |
| | 30 ≤ Capacity | 196 |
| For very small amounts | Capacity < 2 | 490 |
| | 2 ≤ Capacity | 392 |

TABLE 2

| Capacity of syringe barrel (mL) | Liquid sealing test | |
|---|---|---|
| | Example 1 | Comp. Ex. 1 |
| 1 | 0/20 | 2/20 |
| 3 | 0/20 | 3/20 |
| 5 | 0/20 | 2/20 |
| 10 | 0/20 | 2/20 |
| 20 | 0/20 | 1/20 |
| 50 | 0/20 | 1/20 |
| 100 | 0/20 | 2/20 |

(2) Measurement of Sliding Resistance
Plastic (cyclic olefin polymer) made syringe barrels of 1 mL and 3 mL in capacity and rubber-made pistons of sizes corresponding to the respective syringe barrels were provided. Into each rubber-made piston, a plunger (piston rod) was threadedly inserted, and the rubber-made piston with the plunger threadedly inserted therein was fitted in the corresponding syringe barrel. Until a leading end of the rubber-made piston as a sealing plug reached a position where the sealed compartment became equal to the specified capacity of the plastic syringe barrel, the rubber-made piston was slowly pushed into the syringe barrel to provide a sample syringe barrel. A commercially-available disposable injection needle of a specified size was next inserted firmly in a free end portion of the sample syringe barrel. Using a commercially-available syringe with an injection needle fitted thereon, distilled water was injected as much as the specified capacity of the syringe barrel through the free end portion of the sample syringe barrel. At that time, care must be exercised to prevent air from entering the sample syringe barrel. With the free end of the sample syringe barrel directed downwards, the sample syringe barrel was inserted in a metal-made jig. Between spherical-seat-type compression test plates of a compression test instrument equipped with a pressure sensor, "AUTOGRAPH AG-IKND" (trade name, manufactured by Shimadzu Corporation), the rubber-made piston as the sealing plug was pressed at a rate of 100 mm/sec into the sample syringe barrel at the free end thereof. Sliding resistance at that time was measured. From a sliding resistance measurement chart obtained as described above, the maximum value was read and was recorded as a sliding resistance. From the results, no particular difference was observed between the Example and the Comparative Example, and in both the Example and the Comparative Example, the sliding resistance was about 6 N at 1 mL and about 10 N or so at 3 mL.

This application claims the priority of Japanese Patent Application 2004-376478 filed Dec. 27, 2004, which is incorporated herein by reference.

The invention claimed is:

1. A syringe piston composed of a rubber material having a film laminated thereon, wherein said syringe piston comprises a liquid-contacting leading end portion, a trailing end portion opposite said liquid-contacting leading end portion, a sliding surface extending from the liquid-contacting leading end portion to the trailing end portion, and a plurality of annular ridges of different outer diameters formed integrally on the sliding surface at said liquid-contacting leading end portion, and wherein said outer diameters of said plurality of annular ridges sequentially increase, from said liquid-contacting leading end portion toward said trailing end portion, in a manner such that at least one of said plurality of annular ridges has an outer diameter greater than an inner diameter of a syringe barrel configured to receive the syringe piston to retain a sealing property, wherein at least one of said plurality of annular ridges has a larger diameter than the remainder of the sliding surface, and wherein a difference between said outer diameters of adjacent annular ridges is from 0.01 mm to 0.2 mm.

2. The syringe piston according to claim 1, wherein said plurality of annular ridges are two or more annular ridges.

3. The syringe piston according to claim 1, wherein said plurality of annular ridges are three or more annular ridges.

4. The syringe piston according to claim 1, wherein said film is a fluorinated resin.

5. The syringe piston according to claim 4, wherein said fluorinated resin is selected from the group consisting of polytetrafluoroethylene, ethylene-tetrafluoroethylene copolymer, perfluoroalkoxyalkane, perfluoroethylene/propylene copolymer, and polyfluorinated vinylidene.

6. The syringe piston according to claim 1, wherein said rubber material is selected from the group consisting of butyl rubber, chlorinated butyl rubber, brominated butyl rubber, and divinylbenezene-copolymerized butyl rubber.

7. The syringe piston according to claim 1, wherein said rubber material is a diene rubber selected from the group consisting of polyisoprene rubber, polybutadiene rubber, styrene-butadiene copolymerized rubber, and ethylene-propylene-diene terpolymer rubber.

8. The syringe piston according to claim 1, wherein said syringe piston is further composed of an additive selected from the group consisting of a crosslinking agent, a filler, a reinforcement, a colorant, and an age resister.

* * * * *